(12) United States Patent
Kotanko et al.

(10) Patent No.: US 11,419,966 B2
(45) Date of Patent: *Aug. 23, 2022

(54) VIRTUAL PATIENT DONATION

(71) Applicant: Fresenius Medical Care Holdings, Inc., Waltham, MA (US)

(72) Inventors: Peter Kotanko, New York, NY (US); Stephan Thijssen, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 419 days.

This patent is subject to a terminal disclaimer.

(21) Appl. No.: 16/589,581

(22) Filed: Oct. 1, 2019

(65) Prior Publication Data

US 2020/0030516 A1 Jan. 30, 2020

Related U.S. Application Data

(63) Continuation of application No. 16/511,062, filed on Jul. 15, 2019, now Pat. No. 11,273,243, which is a (Continued)

(51) Int. Cl.
*A61M 1/16* (2006.01)
*A61M 1/36* (2006.01)
*A61M 60/00* (2021.01)

(52) U.S. Cl.
CPC ........ *A61M 1/1656* (2013.01); *A61M 1/1623* (2014.02); *A61M 1/1631* (2014.02); (Continued)

(58) Field of Classification Search
CPC .............. A61M 1/1656; A61M 1/1623; A61M 1/1631; A61M 1/1696; A61M 1/3621; (Continued)

(56) References Cited

U.S. PATENT DOCUMENTS 3,682,172 A * 8/1972 Freedman ............ B01D 65/102
604/7
3,699,960 A 10/1972 Freedman
(Continued)

FOREIGN PATENT DOCUMENTS

EP 0615780 B1 4/2001
EP 1547628 A4 2/2008
(Continued)

OTHER PUBLICATIONS

Breimer et al. "Extracorporeal ("ex vivo") connection of pig kidneys to humans. I. Clinical data and studies of platelet destruction," Xenotransplantation, ISSN 0908-665X, 1996; 3rd Issue, pp. 328-339.
(Continued)

*Primary Examiner* — Ariana Zimbouski
(74) *Attorney, Agent, or Firm* — Bass Patent Law, LLC

(57) ABSTRACT

A system includes a device having a blood side, a solution side, and a semipermeable membrane structurally configured for diffusion of one or more solutes therethrough. The system also includes a first extracorporeal circuit having one or more first fluid connectors for connecting the blood side of the device to the vascular system of a first animal, a second extracorporeal circuit including one or more second fluid connectors for connecting the solution side of the device to the vascular system of a second animal, a first pump in fluid communication with at least one of the first and second extracorporeal circuits, and a driver mechanically coupled to the first pump, the driver configured to drive the first pump using energy from an energy source.

20 Claims, 3 Drawing Sheets

Related U.S. Application Data continuation of application No. 15/869,526, filed on Jan. 12, 2018, now Pat. No. 10,391,220.

(52) U.S. Cl.
CPC ........ *A61M 1/1696* (2013.01); *A61M 1/3621* (2013.01); *A61M 1/3639* (2013.01); *A61M 60/00* (2021.01); *A61M 2205/8275* (2013.01); *A61M 2205/8293* (2013.01); *A61M 2250/00* (2013.01)

(58) Field of Classification Search
CPC ............ A61M 1/16; A61M 2205/8275; A61M 2205/8293; A61M 2250/00
See application file for complete search history.

(56) References Cited

U.S. PATENT DOCUMENTS

| | | | |
|---|---|---|---|
| 5,151,082 A * | 9/1992 | Gorsuch | A61M 1/1643 |
| | | | 210/645 |
| 5,628,959 A | 5/1997 | Kross | |
| 6,114,176 A * | 9/2000 | Edgson | C12Q 1/58 |
| | | | 435/12 |
| 8,932,469 B2 | 1/2015 | Childers et al. | |
| 10,086,123 B2 | 10/2018 | Welzel et al. | |
| 2003/0129736 A1 | 7/2003 | Mitrani | |
| 2004/0024342 A1 | 2/2004 | Weitzel et al. | |
| 2006/0041995 A1 * | 3/2006 | Toth | E03D 9/05 |
| | | | 4/217 |
| 2009/0120873 A1 * | 5/2009 | Becker | B01D 65/02 |
| | | | 210/636 |
| 2012/0103902 A1 * | 5/2012 | Childers | A61M 1/166 |
| | | | 210/180 |
| 2013/0199998 A1 | 8/2013 | Kelly et al. | |
| 2014/0284275 A1 | 9/2014 | Boccato et al. | |
| 2017/0173251 A1 | 6/2017 | Doyle et al. | |
| 2017/0173253 A1 | 6/2017 | Funkhouser | |

FOREIGN PATENT DOCUMENTS

| | | | | |
|---|---|---|---|---|
| EP | 1572330 B1 | 11/2010 | | |
| EP | 2380610 A1 | 10/2011 | | |
| WO | 2009094185 A2 | 7/2009 | | |
| WO | WO-2018071869 A1 * | 4/2018 | ......... | A61B 5/02042 |
| WO | 2019139671 A1 | 7/2019 | | |
| WO | 2020062135 A1 | 4/2020 | | |

OTHER PUBLICATIONS

CNIPA, Chinese Application No. 201880079770.6, First Office Action dated Sep. 3, 2021, 14 Pages (Chinese and English Translation).

India Patent Office, IN Application No. 202037009001 Examination Report dated Sep. 9, 2021, 7 pages.

Parabiotic Dialysis: Its Usefulness as an Experimental Tool; J.A. Pauze et al.; Journal of Applied Physiology, vol. 30, No. 3, Mar. 1971.

Parabiotic Dialysis; M. Pavone-Macaluso et al.; From the Department of Physiology, Emory University, Atlanta, Georgia 30322 (Publication No. 620 of the Division of Basic Health Sciences. Supported by grants from the Georgia Heart Association and from U.S. Public Health Service (No. HE-07920).

USPTO, U.S. Appl. No. 16/511,062, Non-Final Office Action dated Oct. 1, 2021. 15 pages.

EPO, Application No. EP18899645.8, Extended European Search Report dated Apr. 7, 2021, 10 Pages.

"Liver support system," Wikipedia, https://en.wikipedia.org/wiki/Liver_support_system, last edited on Feb. 2, 2020. 39 Pages.

"Plasmapheresis," Wikipedia, https://en.wikipedia.org/wiki/Plasmapheresis, last edited on Mar. 20, 2020. 7 pages.

Boada, et al., "Treatment of Alzheimer disease using combination therapy with plasma exchange and haemapheresis with albumin and intravenous immunoglobulin: Rationale and treatment approach of the AMBAR (Alzheimer Management By Albumin Replacement)," Sociedad Española de Neurología, 31: pp. 473-481 (2016).

Fresenius Medical Care, "Prometheus® therapy system for the support of liver function," Product Catalog (2007). 8 Pages.

Fresenius Medical Care, AlbuFlow Filter Spec Sheet (2014). 12 pages.

Gambro, "MARS® system takes over detoxification when the liver can't" (2013). 4 pages.

Lee, et al., "Extracorporeal liver assist device to exchange albumin and remove endotoxin in acute liver failure: Results of a pivotal pre-clinical study," Journal of Hepatology, vol. 63, pp. 634-642 (2015).

Menendez-Gonzalez, et al., "Albumin Exchange in Alzheimer's Disease: Might CSF Be an Alternative Route to Plasma?," vol. 10, Article 1036 (Oct. 2019). 7 pages.

Parabiotic Dialysis: Its Usefulness as an Experimental Tool; J.A. Pauze et al.; Journal of Applied Physiology, vol. 30, No. 3, Mar. 1971. pp. 420-423.

Parabiotic Dialysis; M. Pavone-Macaluso et al.; From the Department of Physiology, Emory University, Atlanta, Georgia 30322 (Publication No. 620 of the Division of Basic Health Sciences. Supported by grants from the Georgia Heart Association and from U.S. Public Health Service (No. HE-07920). pp. 285-291.

WIPO, PCT Application No. PCT/US/2018/061167, Notification Concerning Transmittal of International Preliminary Report on Patentability issued by the International Bureau of WIPO, dated Jul. 23, 2020. 6 Pages.

Safiullah, et al. "Development of a Three-Dimensional Kidney Model for Use in a Virtual Reality Environment." UC Irvine: Clinical Translational Science Day UCI, Jun. 13, 2017 (Jun. 13, 2017).

Horslen, et al. "Extracorporeal Liver Perfusion Using Human and Pig Livers far Acute Liver Failure." Transplantation (online): Nov. 27, 2000 (Nov. 27, 2000)—vol. 70—Issue—p. 1472-1478.

Breimer, et al. "Extracorporeal ("ex vivo") connection of pig kidneys to humans. I. Clinical data and studies of platelet destruction.": Xenotransplantation; Nov. 1996.

Written Opinion and International Search Report of PCT/US18/61167, dated Dec. 5, 2018.

EPO, "Invitation to Pay Additional Fees dated Sep. 29, 2021," PCT Application No. PCT/US21/38192, 15 pages.

USPTO, "U.S. Appl. No. 16/511,062 Notice of Allowance dated Dec. 14, 2021," 7 pages.

ISA/EP, "International Search Report and Written Opinion dated Nov. 19, 2021," PCT Application No. PCT/US21/38192, 18 Pages.

CNIPA, Chinese Application No. 201880079770.6, Second Office Action dated Apr. 29, 2022, English and Chinese translations, 14 pages.

Sun Shilan, et al. ed., "New Theory and New Technology of Hemopurification," Henan Science and Technology Press, 1st Edition, Sep. 20, 2017, English and Chinese translations, 5 pages.

Wu Kaichun et al. ed., China Medical Science Press, 1st Edition, Jun. 30, 2017, English and Chinese translations, 9 pages.

* cited by examiner

VIRTUAL PATIENT DONATION

CROSS-REFERENCE TO RELATED APPLICATIONS

This application is a continuation of U.S. patent application Ser. No. 16/511,062 filed on Jul. 15, 2019, which is a continuation of U.S. patent application Ser. No. 15/869,526 filed on Jan. 12, 2018 (now U.S. Pat. No. 10,391,220), where the entire contents of each of the foregoing applications are hereby incorporated by reference herein.

FIELD

The present disclosure generally relates to virtual kidney donation. In particular, it relates to devices, systems, and methods for hemodialysis with limited resources, such as environments and settings with little or intermittent fresh water and/or energy.

BACKGROUND

In a typical hemodialysis procedure, which is usually conducted in a dialysis outpatient facility or hospital but can be performed at home, a kidney patient's blood is pumped through a dialyzer, where excess water, toxins, or other harmful solutes are removed. Then the processed blood is pumped back into the kidney patient's bloodstream. Specifically, solutes are diffused across the dialyzer's semipermeable membrane into dialysate, where the dialysate flows in the opposite direction to blood flow in an extracorporeal circuit. Ultrafiltration is achieved by controlling the transmembrane pressure, causing water to move across the membrane along a pressure gradient that is created. The dialysate is typically a sterilized solution of mineral ions, where urea and other waste products, potassium, and phosphate diffuse into the dialysate. The dialysate may also include sodium and chloride (similar to those of normal plasma to prevent loss of such solutes), sodium bicarbonate (added to correct blood acidity), and a small amount of glucose. During a typical hemodialysis procedure, which lasts approximately three to four hours, as much as sixty liters or more of fresh water may be used to generate the dialysate required for the session.

In this manner, in a typical hemodialysis procedure, a power source for the pump(s) (e.g., electricity) and fresh water (e.g., for the dialysate) are necessary items without which, dialysis cannot be performed. Thus, dialysis treatments may be unavailable in environments where access to such resources is limited, e.g., regions with developing or unreliable infrastructure (e.g., third-world countries or economically-challenged areas), undeveloped regions, and disaster-stricken areas (e.g., a developed region affected by a natural disaster, military conflict, or the like that has temporarily disabled its infrastructure). There thus remains a need to provide hemodialysis with limited resources.

SUMMARY

In an aspect, a system includes a dialyzer having a blood side and a dialysate side, a first extracorporeal circuit including one or more first fluid connectors for connecting the blood side of the dialyzer to the vascular system of a kidney patient, a second extracorporeal circuit including one or more second fluid connectors for connecting the dialysate side of the dialyzer to the vascular system of a healthy animal, a first pump in fluid communication with at least one of the first and second extracorporeal circuits, and a driver mechanically coupled to the first pump, where the driver is configured to drive the first pump using energy from an energy source.

Implementations may include one or more of the following features. The healthy animal may be a human. The healthy animal may be a non-human. The driver may include a mechanical crank, where the energy source is an animal. The mechanical crank may be a hand crank, where the animal is a human. The driver may include a motor and a photovoltaic cell, where the energy source is light. The driver may include a motor, where the energy source is a battery. The system may further include a second pump. The first pump may be in fluid communication with the first extracorporeal circuit, and the second pump may be in fluid communication with the second extracorporeal circuit. The second pump may be mechanically coupled to the driver. One or more of the first pump, the second pump, and the driver may be configured to establish a predetermined pressure gradient between the first and second extracorporeal circuits. The predetermined pressure gradient may be provided at least in part by a predetermined gear ratio difference between the first pump and the second pump. The system may further include a selector switch having at least a first setting and a second setting, the first setting establishing a zero-pressure gradient between the first and second extracorporeal circuits, and the second setting establishing a nonzero pressure gradient between first and second extracorporeal circuits. The predetermined pressure gradient may be selected to implement ultrafiltration from the first extracorporeal circuit to the second extracorporeal circuit. The system may further include a resistive element in fluid communication with one or more of the first extracorporeal circuit and the second extracorporeal circuit, the resistive element configured to establish a predetermined pressure gradient between the first and second extracorporeal circuits. The dialyzer may include one or more of a hollow-fiber dialyzer and a plate dialyzer. At least one of the one or more first fluid connectors and the one or more second fluid connectors may be primed with an anti-coagulant.

In an aspect, a method for performing hemodialysis includes moving blood of a kidney patient through a first extracorporeal circuit including a first fluid connector that connects a blood side of a dialyzer to the vascular system of the kidney patient, and moving one or more solutes through the dialyzer to a second extracorporeal circuit including a second fluid connector that connects a dialysate side of the dialyzer to the vascular system of a healthy animal.

Implementations may include one or more of the following features. The method may further include establishing a nonzero pressure gradient from the first extracorporeal circuit to the second extracorporeal circuit. One or more solutes moved through the second extracorporeal circuit may include uremic toxins and metabolic waste extracted from the blood of the kidney patient, where the one or more solutes are moved from the dialyzer to the vascular system of the healthy animal for removal via kidney function of the healthy animal. One or more solutes moved through the second extracorporeal circuit may include healthy solutes extracted from the vascular system of the healthy animal and moved to the dialyzer for mixing with the blood of the kidney patient.

In an aspect, a method includes connecting a blood side of a dialyzer to the vascular system of a kidney patient to form a first extracorporeal circuit, and connecting a dialysate side of the dialyzer to the vascular system of a healthy animal to form a second extracorporeal circuit including a second fluid connector.

Implementations may include one or more of the following features. The method may further include establishing a nonzero pressure gradient from the first extracorporeal circuit to the second extracorporeal circuit. The method may further include moving blood of a kidney patient through the first extracorporeal circuit, and moving one or more solutes through the dialyzer to the second extracorporeal circuit.

These and other features, aspects, and advantages of the present teachings will become better understood with reference to the following description, examples, and appended claims.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

DETAILED DESCRIPTION

Figure 1:
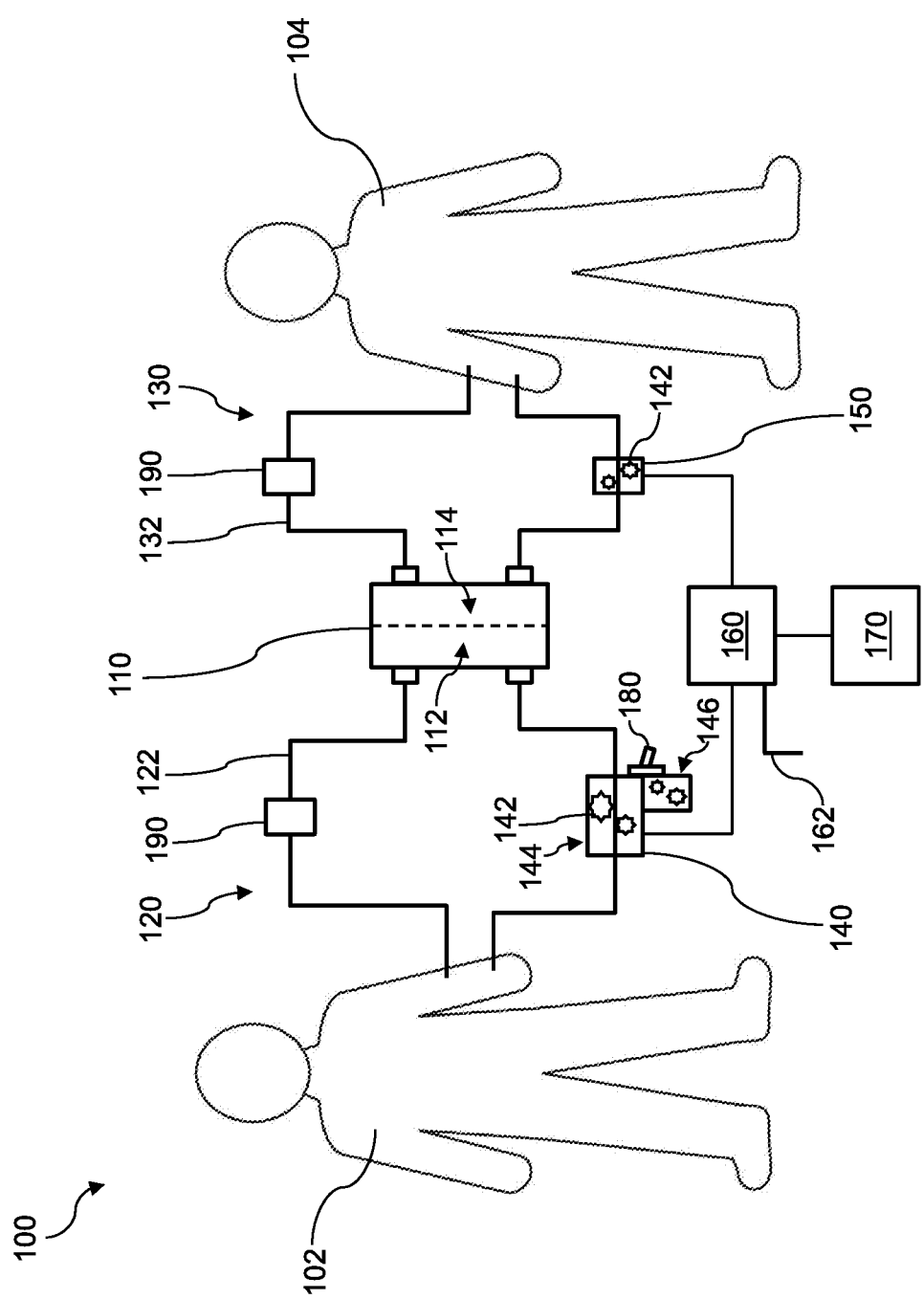
FIG. 1 illustrates a system for hemodialysis with limited resources, in accordance with a representative embodiment.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "about," "approximately," or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms unless specifically stated to the contrary.

In general, the devices, systems, and methods disclosed herein generally relate to hemodialysis. Specifically, the devices, systems, and methods disclosed herein may relate to performing hemodialysis with limited resources such as environments and settings with limited or no availability or access to fresh water (e.g., that can be used for creating dialysate) or energy (e.g., electricity) to run pumps and other dialysis equipment and components. For example, the present teachings may be used in undeveloped, underdeveloped, or disaster-stricken regions for providing hemodialysis to patients. Also, or instead, the present teachings may otherwise be used by patients outside of a treatment facility, e.g., when at home or when traveling.

To this end, the present teachings may include a hemodialysis system that does not require access to grid power to run pumps and other components of the system. Also, or instead, the present teachings may include a system where hemodialysis is performed using a healthy animal (e.g., a person with normal kidney function) to help remove harmful solutes from, and provide helpful solutes to, a kidney patient. In this manner, the dialysate that would be used in a traditional treatment may be replaced by the blood of a healthy animal without a need for a fresh water source. The healthy animal's blood may receive uremic toxins, metabolic waste, and excess water from the kidney patient's blood, which can then be cleared from the healthy animal via its normal kidney function. Thus, the healthy animal is "virtually donating" its kidney function to the kidney patient for the duration of the treatment.

The present teachings may thus include a traditional dialysis configuration (e.g., using a conventional dialyzer connected to a kidney patient in a conventional manner), however, the present teachings may include using a healthy animal with adequate kidney function to eventually remove harmful solutes (e.g., uremic toxins, potassium, phosphate, and so on) and to eventually provide helpful solutes to the kidney patient (e.g., sodium bicarbonate, glucose, and so on). That is, the dialyzer may be connected to the healthy animal's vascular system using the dialysate ports of the dialyzer. In this manner, the typical convective/diffusive processes may occur across a membrane of the dialyzer—uremic toxins and other metabolic waste migrate across the membrane from the kidney patient to the healthy animal. Moreover, ultrafiltration can be accomplished in a conventional manner—by establishing a pressure gradient between the two sides of the dialyzer. The uremic toxins, metabolic waste, and excess water may then be cleared from the healthy animal via its normal kidney function.

FIG. 1 illustrates a system for hemodialysis with limited resources, in accordance with a representative embodiment. As described herein, the system 100 may be used to perform hemodialysis when there is limited (or zero) access to grid power or fresh water. In this manner, the system 100 may be used as an emergency replacement to a standard hemodialysis system. The system 100 may generally include a kidney patient 102, a healthy animal 104, a dialyzer 110, a first extracorporeal circuit 120, a second extracorporeal circuit 130, one or more pumps (e.g., a first pump 140 and a second pump 150 as shown in the figure), one or more drivers 160 for driving the one or more pumps, and an energy source 170 for supplying energy to the one or more drivers 160.

The kidney patient 102 may include a human that has kidney disease (e.g., acute or chronic kidney disease), or has experienced a form of kidney failure, thus needing dialysis treatments. The healthy animal 104 may preferably include a human. The healthy animal 104 may alternatively include a non-human, e.g., a horse, a cow, a sheep, and so on. It will be understood that, although the use of a human as the healthy animal 104 may be preferred, a non-human animal may be preferable to foregoing dialysis treatments entirely. In particular, some blood borne pathogens that are typically found only in animals (e.g., prions that can cause bovine spongiform encephalopathy (BSE), commonly known as mad cow disease) are only about 10-nm in diameter, which is small enough to cross a typical dialyzer membrane. The risk of exposure to these or other blood borne pathogens may be weighed against the risk of foregoing dialysis entirely, on a case by case basis.

The term "healthy" as used herein when describing the healthy animal 104 shall mean that the animal has apparently normal kidney function, where "normal" will be understood to mean kidney function that does not need supplementation or treatment via dialysis or the like. Thus, the term "healthy" when describing the healthy animal 104 shall generally include an animal that has greater than about 15 percent of their kidney function and/or has a glomerular filtration rate (GFR) of greater than about 15.

In the context of the present teachings, the kidney patient 102 can be thought of as simply a first animal, and the healthy animal 104 can be thought of as simply a second animal. The first animal may be any animal where it is desirous to perform dialysis on that animal's blood and return the processed blood to the animal. The second animal may be any animal whose blood contains solutes that are desirous for transfer into the blood of the first animal, and/or any animal that has a kidney function such that solutes transferred from the blood of the first animal will not significantly harm the second animal (e.g., the solutes may be cleared from the second animal via its normal kidney function, i.e., where dilution of the solutes will occur in the second animal without significant adverse effects). Thus, generally, the present teachings may use two living animals that form parts of the first extracorporeal circuit 120 and the second extracorporeal circuit 130 in the system 100.

The dialyzer 110 may be any as known in the art, e.g., a standard "off-the-shelf" dialyzer. For example, the dialyzer 110 may include one or more of a hollow-fiber dialyzer and a plate dialyzer. In general, the dialyzer 110 may include a semipermeable membrane for the diffusion of one or more solutes therethrough.

As such, the dialyzer 110 may include a blood side 112 and a dialysate side 114. The term "dialysate side" is a term of convenience used consistently with standard terminology, and does not indicate an intended use. In particular, this document makes reference to a "dialysate side" of a dialyzer, even when blood of a healthy animal 104 (and not dialysate) is flowing therethrough.

The first extracorporeal circuit 120 may include one or more first fluid lines and/or connectors 122 for connecting the blood side 112 of the dialyzer 110 to the vascular system of the kidney patient 102. In general, the first extracorporeal circuit 120 may provide a fluid path for drawing blood from the kidney patient 102 through the dialyzer 110 and back into the vascular system of the kidney patient 102 thereby providing processed blood to the kidney patient 102. Other than the semi-permeable membrane within the dialyzer 110, the first extracorporeal circuit 120 may be isolated from the second extracorporeal circuit 130 in the system 100.

The first lines and/or fluid connectors 122 may include tubing such as intravenous (IV) tubing made from any suitable material, including without limitation, one or more of polypropylene, nylon, dynaflex, and the like. The first fluid lines and/or connectors 122, or generally the first extracorporeal circuit 120, may also or instead include devices or components used to gain access to the blood of the kidney patient 102 for hemodialysis, including without limitation, one or more of an IV catheter, a synthetic graft, and the like.

The second extracorporeal circuit 130 may include one or more second fluid connectors 132 for connecting the dialysate side 114 of the dialyzer 110 to the vascular system of a healthy animal 104. In general, the second extracorporeal circuit 130 may provide a fluid path for drawing blood from the healthy animal 104 through the dialyzer 110 and back into the vascular system of the healthy animal 104. In this manner, the blood from the healthy animal 104 may act in the role of the dialysate during a traditional HD treatment using the hemodialysis system 100. In other words, one or more solutes may be moved to or from the second extracorporeal circuit 130. These solutes may include unwanted or harmful solutes—uremic toxins, metabolic waste, and excess water extracted from the blood of the kidney patient, or beneficial solutes extracted from the vascular system of the healthy animal 104.

The second fluid connectors 132 may be the same or similar to the first fluid connectors 122. Similarly, the second fluid connectors 132, or generally the second extracorporeal circuit 130, may also or instead include devices or components used to gain access to the blood of the healthy animal 104, including without limitation, one or more of an IV catheter, a synthetic graft, and the like. In some implementations, a preliminary procedure may be performed on the healthy animal 104 to make vascular access more convenient. Such procedures may include, e.g., creating a venous-venous connection, an arterio-arterio connection, an arterio-venous connection including an arterio-venous fistula or graft, inserting an indwelling needle or cannula, a Venflon device or similar, a catheter, a Port-A-Cath device or similar, a peripherally inserted central catheter (PICC), and the like into one or more blood vessels.

In some implementations, the first and/or second fluid connectors 122, 132 may be pre-primed with an anti-coagulant such as heparin. This advantageously reduces the deployment time of the system 100.

As discussed above, the system 100 may include one or more pumps, e.g., a first pump 140 in fluid communication with the first extracorporeal circuit 120 and a second pump 150 in fluid communication with the second extracorporeal circuit 130. In other aspects, the system 100 may include a single pump that is connected to each of the first extracorporeal circuit 120 and the second extracorporeal circuit 130. For example, the system 100 may include a first pump 140 in fluid communication with at least one of the first extracorporeal circuit 120 and the second extracorporeal circuit 130. Whether using a single pump (e.g., the first pump 140), or a plurality of pumps (e.g., the first pump 140 and the second pump 150), the pump(s) may be operable to provide independent, but coordinated, control over the fluid flow in each of the first extracorporeal circuit 120 and the second extracorporeal circuit 130.

One or more of the pumps, e.g., the first pump 140 and the second pump 150, may be connected to one or more drivers 160 for driving the pumps. For example, each pump may be operably (e.g., mechanically) coupled to the same driver 160. In this manner, the first pump 140 and the second pump 150 may be mechanically coupled to the driver 160 as shown in the figure. Alternatively, different pumps in the system 100 may be connected to different drivers 160, but this can complicate the system 100 for establishing a predetermined pressure gradient between the first extracorporeal circuit 120 and the second extracorporeal circuit 130 as discussed herein. Thus, it may be preferable that each pump is mechanically coupled to the same driver 160 in the system 100.

So that ultrafiltration can be performed, one or more of the first pump 140, the second pump 150, and the driver 160 may be configured to establish a predetermined pressure gradient between the first extracorporeal circuit 120 and the second extracorporeal circuit 130. Stated otherwise, the predetermined pressure gradient may be selected to implement ultrafiltration from the first extracorporeal circuit 120 to the second extracorporeal circuit 130.

The predetermined pressure gradient may be provided at least in part by a predetermined gear ratio difference between the first pump 140 and the second pump 150. Further, a gear ratio difference between the first pump 140 and the second pump 150 may be controllable in the system 100. For example, one or more of the first pump 140 and the second pump 150 may include a plurality of gears 142, where different combinations or sets of gears 142 can be selectively used or configured for pumping fluid in the extracorporeal circuits to achieve a predetermined gear ratio and thereby establish a predetermined pressure gradient between the extracorporeal circuits.

To this end, the system 100 may further include one or more selector switches 180. In certain aspects, a selector switch 180 has at least a first setting and a second setting, where the first setting establishes a zero-pressure gradient between the first extracorporeal circuit 120 and the second extracorporeal circuit 130, and where the second setting establishes a nonzero pressure gradient between the first extracorporeal circuit 120 and the second extracorporeal circuit 130. Other settings for different nonzero pressure gradients are also possible using a selector switch 180.

By way of example, the selector switch 180 may be operable to switch between different sets of gears 142 in one or more of the pumps. This is shown by way of representation in the figure, where the first pump 140 includes a first set of gears 144 and a second set of gears 146. The selector switch 180 may be operable to toggle between the first set of gears 144 and a second set of gears 146. In this manner, the selector switch 180 may include a mechanical toggle, a wheel, a slider, a valve, or another similar mechanical input device that switches between sets of gears 142 (or otherwise redirects or adjusts flow) to control a pressure gradient between the first extracorporeal circuit 120 and the second extracorporeal circuit 130 in the system 100. The selector switch 180, or other components in the system 100, may alternatively be electronically operated or controlled.

In implementations, the range of available pressure gradients may fall between those affording a standard clinical range of ultrafiltration rates. For example, pressure gradients resulting in an ultrafiltration rate from 0 L/hour to 1 L/hour may be implemented.

The pumps in the system 100 may include any as known in the art of hemodialysis. For example, one or more of the pumps may include, without limitation, a peristaltic pump (e.g., a roller pump), a syringe pump, a centrifugal pump, and so on. More generally, any pump capable of pumping blood may be used in the system 100. In an aspect, each of the first pump 140 and the second pump 150 include a peristaltic pump; in this manner, it will be understood that the gears 142 described herein and shown in the figure may include rollers or the like instead of "gears" in the traditional sense (e.g., the gears 142 may lack teeth/cogs).

One or more drivers 160 may be used to drive the pumps in the system 100. For example, the driver 160 may be mechanically coupled to the first pump 140, where the driver 160 is configured to drive the first pump 140 using energy from the energy source 170. The driver 160 may similarly be mechanically coupled to the second pump 150, where the driver 160 is configured to drive the second pump 150 using energy from the energy source 170. Thus, the energy source 170 may supply energy to one or more drivers 160 in the system 100.

In implementations, the driver 160 may include a mechanical crank 162, where the energy source 170 is an animal. For example, the mechanical crank 162 may include a hand or foot crank, where the animal is a human that uses the hand or foot crank to create energy for activating the driver 160 to drive the pump(s). In implementations, the driver 160 may include a motor and a photovoltaic cell, where the energy source is light, e.g., sunlight. In some implementations, the driver 160 includes a motor, where the energy source is a battery or the like. The driver 160, energy source 170, or both, may also or instead be integral with one or more of the pumps or another component of the system 100.

Thus, as described herein, the system 100 may be operable without the use of grid power, such that the system 100 could be utilized for hemodialysis when disposed in an area lacking relatively easy access to electricity. Also, because the blood of the healthy animal 104 may be used as the dialysate in the system 100, the system 100 could be utilized for hemodialysis when disposed in an area lacking relatively easy access to fresh water.

The system 100 may further include one or more other hemodialysis components 190. The other hemodialysis components 190 may be disposed on one or more of the first extracorporeal circuit 120 and the second extracorporeal circuit 130, or otherwise disposed in the system 100. The other hemodialysis components 190 may include, without limitation, one or more of a sensor, a pressure monitor (e.g., an arterial pressure monitor, a venous pressure monitor, and the like), an air trap, an air detector, a connector, a valve, a heparin pump, a saline drip (or other drip, or pharmaceutical solution), a reservoir, a heater, a controller, a resistive element, a reducer, and the like. For example, in an aspect, the pressure differential for ultrafiltration may be established by adding resistance (through the use of a hemodialysis component 190 including a resistive element) to the first extracorporeal circuit 120 (e.g., on a blood outlet on the blood side 112 of the dialyzer 110). This may be accomplished, e.g., by partially closing a valve on the first extracorporeal circuit 120. Thus, the hemodialysis component 190 may include a resistive element such as a valve.

Thus, example advantages of the system 100 may include that it can be used without a source of fresh water (or traditional dialysate), and that it can be used without grid power or another external energy source. However, it will be understood that the system 100 may also be supplemented with traditional components in the event that either fresh water (or traditional dialysate) or an external energy source is available. For example, in lieu of mechanically operated drives 160, the system 100 may include electrically-operated drives 160 for the pumps (i.e., the pump(s) may be electrically operated in an embodiment).

Figure 2:
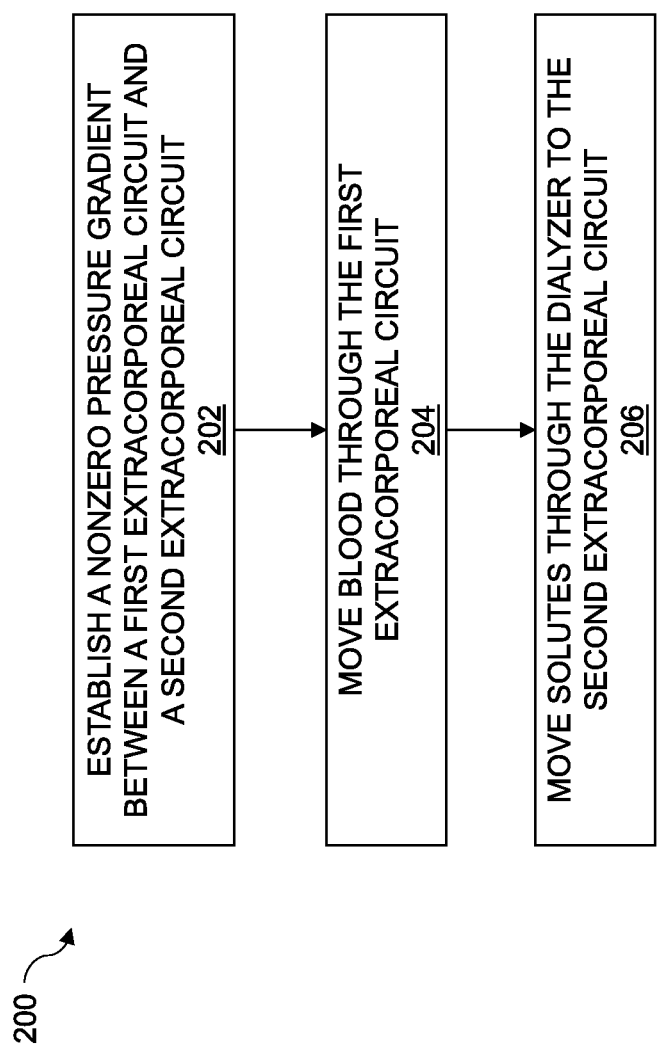
FIG. 2 is a flow chart of a method for performing hemodialysis, in accordance with a representative embodiment.

FIG. 2 is a flow chart of a method for performing hemodialysis, in accordance with a representative embodiment. The method 200 may include the use of a system such as that described in FIG. 1 above, e.g., a hemodialysis system that does not require access to grid power to run the pumps and other components of the system.

As shown in step 202, the method 200 may include establishing a nonzero pressure gradient from a first extracorporeal circuit to a second extracorporeal circuit. The first extracorporeal circuit may include a first fluid connector that connects a blood side of a dialyzer to the vascular system of a kidney patient, and the second extracorporeal circuit may include a second fluid connector that connects a dialysate side of the dialyzer to the vascular system of a healthy animal.

As shown in step 204, the method 200 may include moving blood of a kidney patient through the first extracorporeal circuit, and as shown in step 206, the method 200 may include moving one or more solutes through the dialyzer to the second extracorporeal circuit. The solutes moved through the second extracorporeal circuit may include one or more of uremic toxins, metabolic waste, and excess water extracted from the blood of the kidney patient, where these solutes are moved from the dialyzer to the vascular system of the healthy animal for removal via kidney function of the healthy animal. The solutes moved through the second extracorporeal circuit may also or instead include healthy solutes extracted from the vascular system of the healthy animal and moved to the dialyzer for mixing with the blood of the kidney patient.

Figure 3:
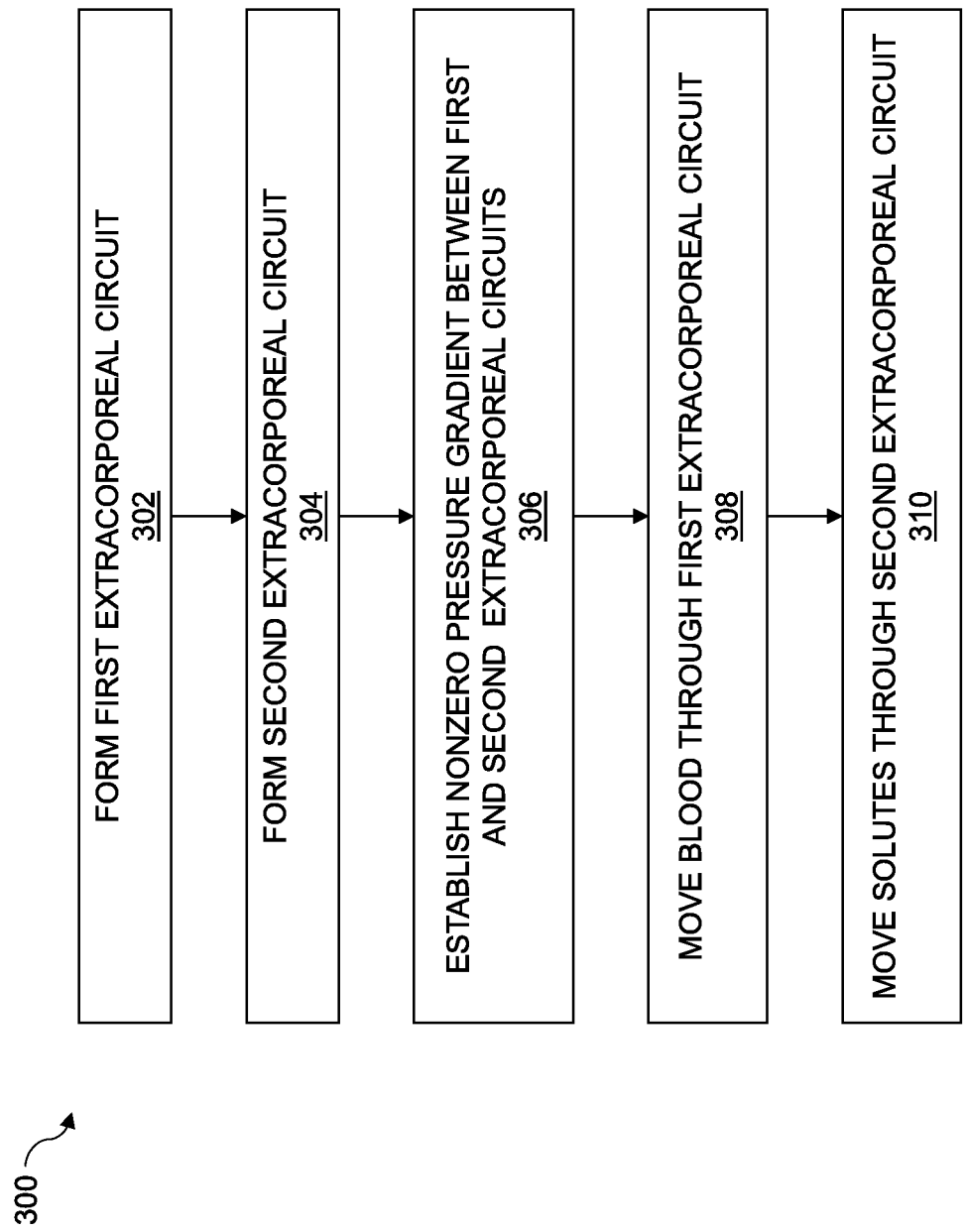
FIG. 3 is a flow chart of a method for hemodialysis, in accordance with a representative embodiment.

FIG. 3 is a flow chart of a method for hemodialysis, in accordance with a representative embodiment. Similar to the method described above with reference to FIG. 2, the method 300 of FIG. 3 may include the use or setup of a system such as that described in FIG. 1 above, e.g., a hemodialysis system that does not require access to grid power to run the pumps and other components of the system.

As shown in step 302, the method 300 may include connecting a blood side of a dialyzer to the vascular system of a kidney patient to form a first extracorporeal circuit.

As shown in step 304, the method 300 may include connecting a dialysate side of the dialyzer to the vascular system of a healthy animal to form a second extracorporeal circuit.

As shown in step 306, the method 300 may include establishing a nonzero pressure gradient from the first extracorporeal circuit to the second extracorporeal circuit.

As shown in step 308, the method 300 may include moving blood of a kidney patient through the first extracorporeal circuit.

As shown in step 310, the method 300 may include moving one or more solutes through the dialyzer to the second extracorporeal circuit.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings.

Unless the context clearly requires otherwise, throughout the description, the words "comprise," "comprising," "include," "including," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A system comprising:
    a device having two sides, a blood side and a solution side, the device including a hollow-fiber semipermeable membrane structurally configured for diffusion of one or more solutes therethrough between the two sides;
    a first extracorporeal circuit including one or more first fluid connectors for connecting the blood side of the device to the vascular system of a first animal;
    a second extracorporeal circuit including one or more second fluid connectors for connecting the solution side of the device to the vascular system of a second animal;
    a first pump in fluid communication with at least one of the first and second extracorporeal circuits; and
    a driver mechanically coupled to the first pump, the driver configured to drive the first pump using energy from an energy source.

2. The system of claim 1, wherein one or more of the first animal and the second animal is a human.

3. The system of claim 1, wherein one or more of the first animal and the second animal is a non-human.

4. The system of claim 1, wherein blood from one or more of the first animal and the second animal contains solutes that are desirous for transfer into blood of the other one of the first animal and the second animal.

5. The system of claim 1, wherein the driver includes a mechanical crank, and wherein the energy source is an animal.

6. The system of claim 5, wherein the mechanical crank is a hand crank, and wherein the animal is a human.

7. The system of claim 1, wherein the driver includes a motor and a photovoltaic cell, and wherein the energy source is light.

8. The system of claim 1, wherein the driver includes a motor, and wherein the energy source is a battery.

9. The system of claim 1, wherein the first pump is in fluid communication with the first extracorporeal circuit and a second pump is in fluid communication with the second extracorporeal circuit, the second pump mechanically coupled to the driver.

10. The system of claim 9, wherein one or more of the first pump, the second pump, and the driver are configured to establish a predetermined pressure gradient between the first and second extracorporeal circuits.

11. The system of claim 10, wherein the predetermined pressure gradient is provided at least in part by a predetermined gear ratio difference between the first pump and the second pump.

12. The system of claim 10, further comprising a selector switch having at least a first setting and a second setting, the first setting establishing a zero-pressure gradient between the first and second extracorporeal circuits, and the second setting establishing a nonzero pressure gradient between the first and second extracorporeal circuits.

13. The system of claim 10, wherein the predetermined pressure gradient is selected to implement ultrafiltration from the first extracorporeal circuit to the second extracorporeal circuit.

14. The system of claim 1, further comprising a resistive element in fluid communication with one or more of the first extracorporeal circuit and the second extracorporeal circuit, the resistive element configured to establish a predetermined pressure gradient between the first and second extracorporeal circuits.

15. The system of claim 1, wherein the device includes a dialyzer.

16. A method for performing solute transfer between animals, the method comprising:
    moving blood of a first animal through a first extracorporeal circuit including a first fluid connector that connects a blood side of a device to the vascular system of the first animal, the device having two sides, the blood side and a solution side, and the device including a hollow-fiber semipermeable membrane structurally configured for diffusion of one or more solutes therethrough between the two sides; and
    moving the one or more solutes through the device to a second extracorporeal circuit including a second fluid connector that connects the solution side of the device to the vascular system of a second animal.

17. The method of claim 16, further comprising establishing a nonzero pressure gradient from the first extracorporeal circuit to the second extracorporeal circuit.

18. A method, comprising:
    connecting a blood side of a device to the vascular system of a first animal to form a first extracorporeal circuit, the device having two sides, the blood side and a solution side, and the device including a hollow-fiber semipermeable membrane structurally configured for diffusion of one or more solutes therethrough between the two sides; and
    connecting the solution side of the device to the vascular system of a second animal to form a second extracorporeal circuit.

19. The method of claim 18, further comprising establishing a nonzero pressure gradient from the first extracorporeal circuit to the second extracorporeal circuit.

20. The method of claim 18, further comprising:
    moving blood of the first animal through the first extracorporeal circuit; and
    moving one or more solutes from the blood of the first animal through the semipermeable membrane to the second extracorporeal circuit.

* * * * *